United States Patent [19]

Phillipps et al.

[11] Patent Number: 4,835,158

[45] Date of Patent: May 30, 1989

[54] ISOQUINOLINE DERIVATIVES

[75] Inventors: Gordon H. Phillipps, Wembley, United Kingdom; Stanley F. Dyke, Samford, Australia; Esme J. Bailey, Richmond, United Kingdom; Peter D. Howes, Pinner, United Kingdom; David I. C. Scopes, Hoddesdon, United Kingdom

[73] Assignee: Glaxo Group Limited, London, England

[21] Appl. No.: 120,654

[22] Filed: Nov. 16, 1987

Related U.S. Application Data

[63] Continuation of Ser. No. 919,007, Oct. 15, 1986, abandoned, which is a continuation of Ser. No. 730,198, May 3, 1985, abandoned.

[30] Foreign Application Priority Data

May 3, 1984 [GB] United Kingdom ................. 8411408
May 3, 1984 [GB] United Kingdom ................. 8411407

[51] Int. Cl.$^4$ .................... A61K 31/47; C07D 471/04; C07D 471/14
[52] U.S. Cl. .................... 514/279; 514/283; 546/41; 546/42; 546/51
[58] Field of Search ............. 546/41, 42, 51; 514/279, 283

[56] References Cited

U.S. PATENT DOCUMENTS

| | | | |
|---|---|---|---|
| 3,336,317 | 8/1967 | Inman et al. | 546/42 |
| 4,033,966 | 7/1977 | Sawa | 546/48 X |
| 4,042,591 | 8/1977 | Kaul | 546/42 |
| 4,087,426 | 5/1978 | Shamma et al. | 546/48 |
| 4,399,282 | 8/1983 | Miyasaka et al. | 546/48 |
| 4,434,290 | 2/1984 | Bisagni et al. | 546/70 |
| 4,444,776 | 4/1984 | Bisagni et al. | 514/287 |

FOREIGN PATENT DOCUMENTS

| | | | |
|---|---|---|---|
| 0161102 | 11/1985 | European Pat. Off. | 514/283 |
| 2129799 | 5/1984 | United Kingdom | 546/42 |

OTHER PUBLICATIONS

Hershenson, J. Organic Chemistry, vol. 37, No. 20, pp. 3111-3113, (1972).
Uchida et al., J. Heterocyclic Chemistry, vol. 15, pp. 1303-1307, (12/78).
Spray, PhD Thesis, University of Bath, England, (1980), pp. 208-221, 243.
Fieser et al., "Reagents for Organic Synthesis", John Wiley & Sons, New York, (1967), pp. 682-684.

Primary Examiner—Nicholas S. Rizzo
Assistant Examiner—Diana G. Rivers
Attorney, Agent, or Firm—Bacon & Thomas

[57] ABSTRACT

Pharmaceutical compositions for combatting cancer comprising a compound of formula (I)

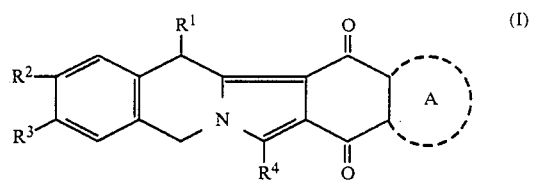

(wherein
$R^1$ represents a hydrogen atom or a $C_{1-4}$ alkyl, $C_{2-4}$ alkenyl or $C_{2-4}$ alkynyl group;
$R^2$ represents a hydrogen atom or a hydroxyl, $C_{1-4}$ alkoxy or $C_{2-4}$ alkanoyloxy group;
$R^3$ represents a hydrogen atom, or (when $R^2$ is other than a hydrogen atom) optionally a hydroxyl, $C_{1-4}$ alkoxy or $C_{2-4}$ alkanoyloxy group, or $R^2$ and $R^3$ together represent a methylenedioxy group;
$R^4$ represents a hydrogen or halogen atom or a $C_{1-3}$ alkyl group or a phenyl group optionally substituted by a halogen atom or a hydroxy, $C_{1-4}$ alkyl, $C_{1-4}$ alkoxy or $C_{1-4}$ alkanoyloxy group; and the ring A represents a group of formula

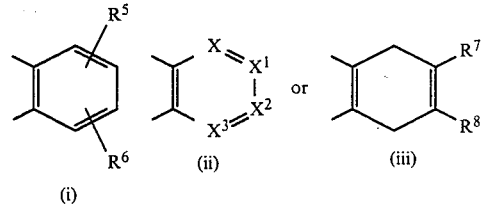

where
$R^5$ and $R^6$ each represent a hydrogen atom or a hydroxyl, $C_{1-4}$ alkoxy or $C_{1-4}$ alkanoyloxy group,
$R^7$ and $R^8$ each represents a hydrogen atom or a methyl group, and one of X, $X^1$, $X^2$ and $X^3$ represents a nitrogen atom and the others represent —CH— groups; with the proviso that where A represents a group of formula (i) at least one of $R^1$ to $R^6$ represents other than a hydrogen atom) together with at least one pharmaceutical carrier or excipient.

6 Claims, No Drawings

ISOQUINOLINE DERIVATIVES

This application is a continuation of application Ser. No. 919,007, filed Oct. 15, 1986, now abandoned, which is a continuation of Ser. No. 730,198, filed May 3, 1985, now abandoned.

This invention relates to new isoquinoline derivatives, to processes for their preparation, to pharmaceutical preparations containing them, and to their use in medicine.

In a thesis by C. R. Spray submitted to the University of Bath, England in 1980, the preparation of 5,14-dihydro-7-methylbenz[5,6]isoindolo[2,1-b]isoquinoline-8,13-dione is described, however bno physiological activity was ascribed to the compound so prepared.

In copending European Patent Application Publication No. 108620 there is disclosed and claimed 5,14-dihydrobenz[5,6]isoindolo[2,1-b]isoquinoline-8,13-dione. We have now found that certain other isoquinoline derivatives possess desirable anticancer activity.

According to one aspect of the invention we thus provide a pharmaceutical composition comprising a compound of general formula (I)

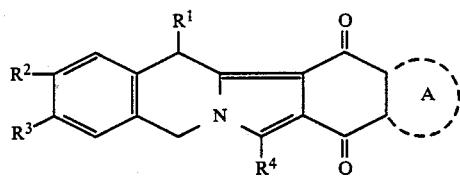

(wherein
$R^1$ represents a hydrogen atom or a $C_{1-4}$ alkyl, $C_{2-4}$ alkenyl or $C_{2-4}$ alkynyl group;
$R^2$ represents a hydrogen atom or a hydroxyl, $C_{1-4}$ alkoxy or $C_{2-4}$ alkanoyloxy group;
$R^3$ represents hydrogen atom, or (when $R^2$ is other than a hydrogen atom) optionally a hydroxyl, $C_{1-4}$ alkoxy or $C_{2-4}$ alkanoyloxy group, or $R^2$ and $R^3$ together represent a methylenedioxy group;
$R^4$ represents a hydrogen or halogen atom or a $C_{1-3}$ alkyl group or a phenyl group optionally substituted by a halogen atom or a hydroxy, $C_{1-4}$ alkyl, $C_{1-4}$ alkoxy or $C_{1-4}$ alkanoyloxy group; and
the ring A represents a group of formula

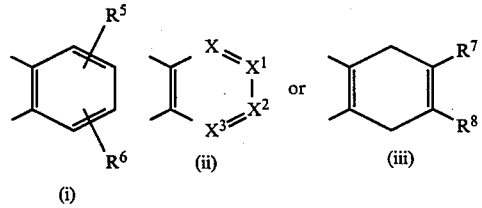

where $R^5$ and $R^6$ each represents a hydrogen atom or a hydroxyl, $C_{1-4}$ alkoxy or $C_{1-4}$ alkanoyloxy group, $R^7$ and $R^8$ each represents a hydrogen atom or a methyl group, and one of X, $X^1$, $X^2$ and $X^3$ represents a nitrogen atom and the others represent —CH— groups; with the proviso that where A represents a group of formula (i) at least one of $R^1$ to $R^6$ represents other than a hydrogen atom) together with at least one pharmaceutical carrier or excipient.

According to a further aspect of the invention we provide compounds of general formula (I) (wherein $R^1$, $R^2$, $R^3$, $R^4$, and A are as hereinbefore defined, with the proviso that where A represents a group of formula (i) and $R^1$, $R^2$, $R^3$, $R^5$ and $R^6$ represent hydrogen atoms, $R^4$ represents a halogen atom, a $C_{2-3}$ alkyl group or a phenyl group optionally substituted by a halogen atom or a hydroxy, $C_{1-4}$ alkyl, $C_{1-4}$ alkoxy or $C_{1-4}$ alkanoyloxy group).

In one particular group of compounds of formula I $R^4$ represents a halogen atom, a $C_{2-3}$ alkyl group or a phenyl group optionally substituted by a halogen atom or a hydroxy, $C_{1-4}$ alkyl, $C_{1-4}$ alkoxy or $C_{1-4}$ alkanoyloxy group and $R^1$ represents a hydrogen atom.

Compounds of formula (I) may exist as stereoisomers and/or tautomers, and the invention is to be understood to include all such isomers of compounds of formula (I), including mixtures thereof.

In general formula (I), the group $R^1$ may be for example a hydrogen atom or a methyl, ethyl, n-propyl, isopropyl, 1-porpenyl, 2-propenyl, 1-propynyl or 2-propynyl group, but preferably is a hydrogen atom or a methyl group.

The group $R^2$ may be for example a hydrogen atom or a hydroxyl, methoxy, ethoxy or acetyloxy group, but preferably is a hydrogen atom. When $R^3$ is a $C_{1-4}$ alkoxy or $C_{2-4}$ alkanoyloxy group, it may be for example a methoxy, ethoxy or acetyloxy group; however $R^3$ preferably is a hydrogen atom.

Examples of the groups represented by $R^4$ are a hydrogen, fluorine, chlorine, bromine or iodine atom, or an ethyl, n-propyl, isopropyl or phenyl group, or a phenyl group substituted by a bromine, chlorine, fluorine or iodine atom, or a hydroxyl, methyl, ethyl, methoxy, ethoxy or acetyloxy group; $R^4$ however preferably represents a hydrogen or bromine atom or a methyl group.

The groups $R^5$ and $R^6$ may each be for example a hydrogen atom or a hydroxyl, methoxy or acetyloxy group, preferably a hydrogen atom or a hydroxyl group.

When the ring A in formula (I) represents a ring of type (i), it may be for example

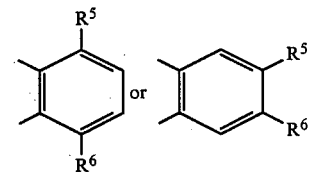

where $R^5$ and $R^6$ are as defined for general formula (I).

Examples of compounds particularly useful according to the invention are those in which $R^1$ represents a hydrogen atom or a methyl group, $R^2$ represents a hydrogen atom, $R^3$ represents a hydrogen atom, $R^4$ represents a hydrogen or bromine atom or a methyl group, and the ring A represents a group of formula

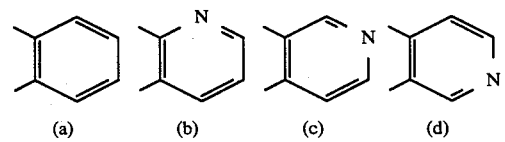

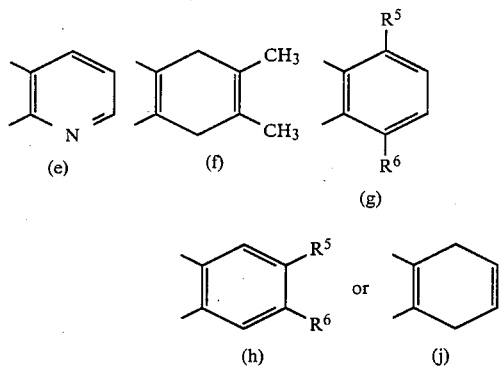

where one of $R^5$ and $R^6$ represents a hydrogen atom or a hydroxyl, methoxy or acetyloxy group, and the other represents a hydroxyl, methoxy or acetyloxy group.

Ring A preferably represents a group of formula (a), (g) or (j) as above.

Particularly preferred compounds according to the invention include compounds having the formula (Ia)

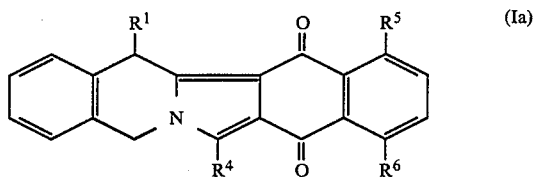

(wherein $R^1$, $R^4$, $R^5$ and $R^6$ are as defined above, and especially wherein $R^1$ represents a hydrogen atom or a methyl group; $R^4$ represents a hydrogen or bromine atom or a methyl group; and $R^5$ and $R^6$, which may be the same or different, each represents a hydrogen atom or a hydroxyl, methoxy or acetyloxy group).

Particularly interesting among the compounds of formula (I) are:
(a) 5,14-dihydro-14-methylbenz[5,6]isoindolo[2,1-b]isoquinoline-8,13-dione;
(b) 5,14-dihydro-9-hydroxybenz[5,6]isoindolo[2,1-b]isoquinoline-8,13-dione;
(c) 5,14-dihydro-12-hydroxybenz[5,6]isoindolo[2,1-b]isoquinoline-8,13-dione;
(d) 5,14-dihydro-9-methoxybenz[5,6]isoindolo[2,1-b]isoquinoline-8,13-dione;
(e) 5,14-dihydro-12-methoxybenz[5,6]isoindolo[2,1-b]isoquinoline-8,13-dione;
(f) 7-bromo-5,14-dihydrobenz[5,6]isoindolo[2,1-b]isoquinoline-8,13-dione;
(g) 9,12-bis(acetyloxy)-5,14-dihydrobenz[5,6]isoindolo[2,1-b]isoquinoline-8,13-dione;
(h) 5,9,12,14-tetrahydrobenz[5,6]isoindolo[2,1-b]isoquinoline-8,13-dione; and
(i) 5,14-dihydro-9,12-dihydroxybenz[5,6]isoindolo[2,1-b]isoquinoline-8,13-dione.

Pharmaceutical compositions containing such compounds are thus preferred as are compositions containing 5,14-dihydro-7-methylbenz[5,6]isoindolo[2,1-b]isoquinoline-8,13-dione.

The compounds of formula (I) possess anticancer activity, particularly against tumours such as sarcomas, carcinomas and hepatomas.

Thus, when a compound of formula (I) is administered intraperitoneally or intravenously to mice with a subcutaneous tumour arising from an implant of S180 cells, subsequent examination has shown that tumour growth has been significantly reduced and in some cases total regression of the tumour has occured.

According to a further aspect of the present invention we therefore provide a compound of formula (I) for use in the treatment of the human or non-human animal body to combat cancer, particularly tumours, therein.

According to a yet further aspect of the present invention we provide the use of a compound of formula (I) for the treatment of the human or non-human animal body to combat cancer, particularly tumours, therein.

According to a still further aspect of the present invention we provide the use of a compound of formula (I) for the manufacture of a therapeutic agent for the treatment of the human or non-human animal body to combat cancer, particularly tumours, therein.

According to a still further aspect of the present invention we provide a method of treatment of the human or non-human animal body to combat cancers, particularly tumours, therein, which method comprises administering to the said body an effective amount of a compound of formula (I).

According to a yet still further feature of the present invention we provide a process for the preparation of a pharmaceutical composition comprising admixing a compound of formula (I) together with one or more pharmaceutical carriers or excipients.

For pharmaceutical administration a compound of general formula (I) may be incorporated into conventional preparations in either solid or liquid form.

The compositions may, for example, be presented in a form suitable for oral, rectal, topical or, more preferably, parenteral administration. Suitable forms include, for example, tablets, capsules, granules, suppositories, creams, ointments and lotions and more particularly suspensions and/or solutions for injection or infusion. Where suspensions are desired, these advantageously may be prepared using a compound of formula (I) in a finely divided, e.g. microcrystalline form.

The active ingredient may be incorporated in excipients customarily employed in pharmaceutical compositions such as, for example, talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and/or preservatives.

Advantageously the compositions may be formulated as dosge units, each unit being adapted to supply a fixed dose of the compound of formula (I). Suitable dosage units for adults contain from 50 to 1000 mg of the compound of formula (I). The dosage, which may be varied according to the particular patient to be treated and complaint concerned, may, for example, be from 0.25 to 7.0 g in a day in adults.

The compounds useful according to the invention may be prepared by a number of processes, as described in the following wherein the various groups and symbols are as defined for formula (I) unless otherwise specified. In the general processes described, hydroxyl groups, where present, may need to be in a protected form and the final step in a process may thus be the removal of a protecting group. The protecting group may be any conventional hydroxyl protecting group, such as an acyl group. Standard protection procedures may be used, for example reaction with an acid or an activated derivative thereof e.g. an acid chloride, in the presence of a base such as triethylamine or pyridine. Deprotection may be effected by acid hydrolysis, using for example an aqueous mineral acid e.g. aqueous hydrochloric acid. Where mixtures of isomers are obtained using the following processes, individual isomers may be separated therefrom by conventional means, for example by chromatography using e.g. silica gel.

According to one general process, a compound of formula (I) in which $R^4$ is a hydrogen atom or an alkyl or optionally substituted phenyl group, may be prepared by condensing a compound of formula (II)

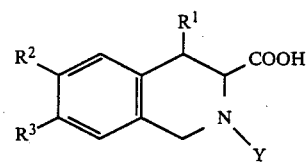

(wherein Y is a group

where $R^4$ is as just defined), or a hydroxyl protected derivative thereof, with a quinone of formula (III)

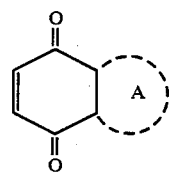

(wherein A is as defined above), or a hydroxyl protected derivative thereof, under carboxyl group activating conditions and subsequently, if necessary, removing any protecting group used. Thus, for example, the process may be carried out in the presence of an alkanoic acid anhydride, such as acetic acid anhydride, optionally in the presence of a solvent, e.g. a hydrocarbon solvent such as toluene. The process may for example be carried out with heating, at e.g. 80°-120° C.

In one convenient embodiment of this process, the starting material may be a compound of formula (II) in which Y represents a hydrogen atom. Reaction of this with a quinone of formula (III) in the presence of an acid anhydride $(R^4CO)_2O$ (where $R^4$ is as just defined, but is not a hydrogen atom) yields a compound of formula (I) in which $R^4$ is an alkyl or optionally substituted phenyl group.

The intermediate compounds of formulae (II) and (III) are either known compounds, or may be prepared by methods analogous to those used for the preparation of the known compounds.

In another process, a compound of formula (I) (wherein $R^1$ is other than hydrogen) may be prepared by reacting a copound of formula (IV)

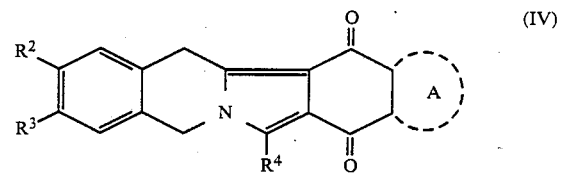

(wherein $R^2$, $R^3$, $R^4$ and A are as defined above), or a hydroxyl protected derivative thereof, with a compound of formula $R^1L$ (where L is a displaceable leaving group such as a halogen atom, e.g. a chlorine, bromine or iodine atom, or a hydrocarbylsulphonyloxy group such as methylsulphonyloxy or p-toluenesulphonyloxy, and $R^1$ is as defined above but does not represent a hydrogen atom) in the presence of a base (such as sodium hydride or potassium carbonate), conveniently in a solvent such as acetonitrile, dichloromethane or dimethylformamide, and optionally in the presence of a phase transfer catlyst such as benzyl triethylammonium chloride, and subsequently, if necessary, removing any protectiong group used.

The intermediate compounds of formula (IV) may be prepared by condensation of an appropriate tetrahydroisoquinoline carboxylic acid and an appropriate quinone as described previously for the preparation of compounds of formula (I).

Another process for the preparation of a compound of formula (I) comprises interconverting another compound of general formula (I). For example, a compound of formula (I) in which $R^4$ is a halogen atom may be prepared by halogenating a corresponding compound in which $R^4$ is a hydrogen atom. Standard procedures may be used, for example reaction with a N-chloro, N-bromo or N-iodoimide e.g. N-chloro-, N-bromo- or N-iodosuccinimide, in the presence of an acid such as sulphuric acid in an aqueous solvent, or by reaction with perchloryl fluoride.

In another example, a compound of formula (I) in which $R^2$, $R^5$ and/or $R^6$ is a hydroxyl group may be prepared by hydrolysing a corresponding compound in which $R^2$, $R^5$ and/or $R^6$ is an alkanoyloxy group. Conventional hydrolysis procedures may be used, for example acid hydrolysis using an aqueous mineral acid such as aqueous hydrochloric acid or an organic acid such trifluoroacetic acid. In this instance the alkanoyloxy group is effectively acting as a protected hydroxyl group.

In a further example, a compound of formula (I) in which $R^2$, $R^5$ and/or $R^6$ is an alkoxy group may be prepared by alkylating a corresponding compound in which $R^2$, $R^5$ and/or $R^6$ is a hydroxyl group. Conventional alkylation procedures may be used, e.g. by reaction with an alkylating agent $R^2L$, $R^5L$ or $R^6L$ (wherein L is as defined above) using the conditions described above for reaction of the intermediates of formula (IV).

In yet another example, a compound of formula (I) in which $R^2$, $R^5$ and/or $R^6$ is an alkanoyloxy group may be prepared by acylating a corresponding compound in which $R^2$, $R^5$ and/or $R^6$ is a hydroxyl group. Conventional acylation procedures may be used, for example reaction with an appropriate acid $R^2$-, $R^5$- or $R^6COOH$ (where $R^2$, $R^5$ or $R^6$ are $C_{1-3}$ alkyl) or an activated derivative thereof e.g. an acid chloride or acid anhydride in the presence of a base such as triethylamine or pyridine.

The following non-limiting Examples illustrate the invention.

Intermediate 1

5,14-Dihydrobenz[5,6]isoindolo[2,1-b]isoquinoline-8,13-dione

A mixture of 2-formyl-3-carboxyl-1,2,3,4-tetrahydroisoquinoline (17.50 g) and 1,4-naphthoquinone (26.95 g) in acetic anhydride (437 ml) was heated at 100° C. with stirring for 30 min. The reaction mixture was cooled and the solid collected by filtration, washed with ether and dried.

Recrystallisation from chloroform/methylene chloride gave the title compound (11.13 g), $\lambda_{max}$ (ethanol) 245 ($\epsilon$43,700), 265 ($\epsilon$14,100) and 368 nm ($\epsilon$5,200).

EXAMPLE 1

5,14-Dihydro-7-phenylbenz[5,6]isoindolo[2,1-b]isoquinoline-8,13-dione

A mixture of 2-benzoyl-1,2,3,4-tetrahydro-3-isoquinoline carboxylic acid (6.0 g) and 1,4-naphthalenedione (6.75 g) in acetic anhydride (240 ml) was stirred at about 100° C. for 20 minutes. The reaction mixture was allowed to stand at room temperature for 48 hours, and the green solid (7.16 g) was collected by filtration. The crude product was recrystallised from chloroform-petroleum ether (b.b. 40°–60° C.) to give the title compound (5.04 g) m.p. 267° C. (decomp), $\lambda_{max}$ (in ethanol) 246.5 nm ($\epsilon$45,500), 320 nm ($\epsilon$2,440), 388 nm ($\epsilon$6,120).

EXAMPLE 2

5,14-Dihydro-2-hydroxy-7-methylbenz[5,6]isoindolo[2,1-b]isoquinoline-8,13-dione

A mixture of 6-hydroxy-1,2,3,4-tetrahydroisoquinoline-3-carboxylic acid (2 g) and 1,4-naphthalenedione (3.4 g) in acetic anhydride (150 ml) was stirred in an oil bath at 100° C. for 15 minutes. It was then allowed to cool to room temperature and the green solid (2.74 g) was collected by filtration, washed with acetic anhydride and ether and dried at 100° C. for 2 h in vacuo, to give the title compound m.p. 275°–320° C. (decomp), $\lambda_{max}$ (in ethanol) 244.5 nm ($\epsilon$26,220) 318 nm ($\epsilon$4,510) and 383 nm ($\epsilon$6,390).

EXAMPLE 3

8,13-Dihydro-6-methylpyrrolo[1,2-b:4,3-g¹]diisoquinoline-5,14-dione and/or
6,11-dihydro-13-methylprrolo[1,2 b:3,4-g¹]diisoquinoline-5,14-dione A mixture of 1,2,3,4-tetrahydro-3-isoquinoline carboxylic acid (5.57 g) and 5,8-isoquinolinedione (10.00 g) in acetic anhydride (130 ml) was stirred for 15 minutes at about 100° C. The suspension was allowed to stand at room temperature for 90 minutes, the green product collected by filtration, washed with diethyl ether to remove the purple colour associated with the filtrate and dried. The crude product (8.22 g) was recrystallised from chloroform-petroleum ether (b.p. 40°–60° C.) and dried in vacuo at 120° C. to give the title compound (5.96 g) m.p. 220° C. (decomp), $\lambda_{max}$ (in ethanol) 231.5 nm ($\epsilon$29,770) 295 nm ($\epsilon$5,120), 399 nm ($\epsilon$5,940).

EXAMPLE 4

(a)
5,14-Dihydro-9-hydroxybenz[5,6]isoindolo[2,1-b]isoquinoline-8,13-dione and
5,14-dihydro-12-hydroxybenz[5,6]isoindolo[2,1-b]isoquinoline-8,13-dione A mixture of 2-formyl-1,2,3,4-tetrahydro-3-isoquinoline carboxylic acid (20 g) and 5-hydroxy-1,4-naphthalenedione (33.90 g) in acetic anhydride (300 ml) was stirred at about 100° C. (bath temperature) for 15 minutes. A green precipitate was seen, and the suspension was allowed to stand at room temperature for 1.5 h before the product (22.76 g) was collected by filtration, washed with acetic anhydride (300 ml) and dried at 100° C. in vacuo. The crude product (5 g portion) was recrystallised from chloroform-petroleum ether (b.p. 40°–60° C.) to give a mixture of the title compounds (3.7 g) m.p. 242° C. (decomp). $\lambda_{max}$ (in ethanol) 244.5 nm ($\epsilon$34,020), 269 nm ($\epsilon$13,370), 397 nm ($\epsilon$11,860).

A portion of the crude product (3 g) was dissolved in chloroform and chromatographed on silica gel. Elution with chloroform then chloroform containing 1% ethyl acetate gave (b) 5,14-dihydro-9-hydroxybenz[5,6]isoindolo[2,1-b]isoquinoline-8,13-dione (350 mg), m.p. >265° C. (decomp) $\lambda_{max}$ (in ethanol) 243 nm ($\epsilon$33,000), 267 mm ($\epsilon$13,800 and (c) 5,14-dihydro-12-hydroxybenz[5,6]isoindolo-[2,1-b]isoquinoline-8,13-dione (798 mg), m.p. >260° C. (decomp) $\lambda_{max}$ 243 nm ($\epsilon$34,500) 268 nm ($\epsilon$13,400).

EXAMPLE 5

9,12-Bis(acetyloxy)-5,14-dihydrobenz[5,6]isoindolo[2,1-b]isoquinoline-8,13-dione 5,8-bis(acetyloxy)-1,4-napthalenedione (4.28 g) and 2-formyl-1,2,3,4-tetrahydro-3-isoquinoline carboxylic acid (1.60 g) in acetic anhydride (65 ml) were heated at 100° C. (20 minutes). The reaction mixture was cooled at about 20° C. (1 h), and the solid was collected by filtration, washed with ether (3×30 ml) and dried in vacuo. The crude product was dissolved in dichloromethane and the solution was loaded onto a column of silica gel (175 g) packed in dichloromethane. The column was eluted with 5% (v/v) ethyl acetate in dichloromethane and fractions containing the major component were evaporated to dryness, and further dried in vacuo at 55° C. to give the title compound as a yellow-green solid (1.34 g), m.p. 228°–232° C. (dec), $\lambda_{max}$ (in CH$_2$Cl$_2$) 242 nm ($\epsilon$40,700), 377 nm ($\epsilon$6,400).

EXAMPLE 6

7-Bromo-5,14-dihydrobenz[5,6]isoindolo[2,1-b]isoquinoline-8,13-dione

A mixture of Intermediate 1 and N-bromosuccinimide (89 mg) in dichloromethane (25 ml) was stirred at room temperature for 1 h. Dichloromethane (50 ml) was added and the mixture was filtered. Removal of solvent under reduced pressure gave a residue which was extracted with ethanol to remove succinimide. The mixture was filtered and the yellow-green solid was dried in vacuo to give the title compound (0.155 g), m.p. >320° C. $\lambda_{max}$ (in CHCl$_3$) 246.5 nm ($\epsilon$52,850) 266 nm ($\epsilon$15,540) and 376.5 nm ($\epsilon$6,880).

EXAMPLE 7

5,9,12,14-Tetrahydrobenz[5,6]isoindolo[2,1-b]isoquinoline-8,13-dione

Light was excluded from the reaction vessel by wrapping in silver foil. 5,8-dihydro-1,4-napthalenedione (2.25 g) and 2-formyl-1,2,3,4-tetrahydro-3-isoquinoline carboxylic acid in acetic anhydride (50 ml) were heated at 100° C. for 15 minutes. The reaction mixture was cooled to 20° C. (1 h). The solid was isolated by filtration, washed with ether and dried in vacuo to give the crude product (1.81 g).

20% (w/w) silver nitrate on silica gel was prepared by adding silver nitrate (24.4 g) in acetonitrile (350 ml) to silica gel (126 g). The acetonitrile was removed under reduced pressure and the residue was dried in vacuo at about 20° C. (17 h).

The crude product (805 mg) in dichloromethane (200 ml) was loaded onto a column of 20% silver nitrate on silica gel (70 g) packed in dichloromethane. After elution of an impurity the product was eluted with 10% (v/v) ethyl acetate in dichloromethane.

Removal of solvent from the eluate gave the title compound as a yellow-green solid (738 mg), m.p. 250°–254° C. (dec); $\lambda_{max}$ (CH$_2$Cl$_2$) 250 nm ($\epsilon$14,200), 384 nm ($\epsilon$5,000).

EXAMPLE 8

10 (and 11)-(Acetyloxy)-5,14-dihydrobenz[5,6]isoindolo[2,1-b]isoquinoline-8,13-dione 6-acetyloxy-1,4-naphthalenedione (5.31 g) and 2-formyl-1,2,3,4-tetrahydro-3-isoquinolinecarboxylic acid (2.53 g) in acetic anhydride (120 ml) were heated at 95° C. (25 minutes). The reaction mixture was allowed to stand at about 20° C. (2 h). The product was collected by filtration, washed with ether (2×50 ml) and dried in vacuo to yield the title compound (17) as a green solid (3.28 g), m.p. 235°–240° C. (dec); $\lambda_{max}$(in CH$_2$Cl$_2$) 248.5 nm ($\epsilon$48,800), 267 nm ($\epsilon$18,300), 367,5 nm ($\epsilon$5,840). By high pressure liquid chromatography, the product was a mixture of isomers in the ratio of about 3:1.

EXAMPLE 9

(a) 5,14-Dihydro-9 (and 12)-methoxybenz[5,6]isoindolo[2,1-b]isoquinoline-8,13-dione To 5-methoxy-1,4-naphthalenedione (10.05 g) and 2-formyl-1,2,3,4-tetrahydro-3-isoquinoline carboxylic acid (5.48 g) was added acetic anhydride (250 ml). The reaction mixture was heated at 100° C. (25 minutes) and was then allowed to cool to about 20° C. over 2.25 h. The product was collected by filtration, washed with ether (2×50 ml) and dried in vacuo to yield a yellow-green solid (55.47 g).

On leaving the mother liquors to stand at about 20° C. (4 days) a further crop of crude product was obtained. This was collected by filtration, washed with ether (2×25 ml) and dried in vacuo to yield a yellow-green solid (1.23 g).

The crude product could be seen by thin layer chromatography (silica, 5% (v/v) ethyl acetate in chloroform) to contain two components, the 9- and 12-methoxy isomers (R$_f$=0.14) and (R$_f$=0.35). The crude product in chloroform was loaded onto a silica gel column packed in chloroform. The column was eluted with 5% (v/v) ethyl acetate in chloroform. The separated isomers were obtained as follows:

(b) 9 (or 12)-methoxy isomer, a yellow solid (2.81 g); m.p. 246°–251° C. (dec); $\lambda_{max}$ (in CH$_2$Cl$_2$) 242.5 nm ($\epsilon$43,00), 371 nm ($\epsilon$11,300).

(c) 12 (or 9)-methoxy isomer, a yellow-green solid (1.13 g); m.p. 227°–230° C. (dec); $\lambda_{max}$(in CH$_2$Cl$_2$) 242.5 nm ($\epsilon$39,000), 375 nm ($\epsilon$9,450).

EXAMPLE 10

5,14-Dihydro-7-methylbenz[5,6]isoindolo[2,1-b]isoquinoline-8,13-dione

A mixture of 1,2,3,4-tetrahydro-3-isoquinoline carboxylic acid hydrochloride (4.0 g) and 1,4-naphthoquinone (5.5 g) in acetic anhydride (115 ml) was heated at 100° C. with stirring for 5.5 hours. The reaction mixture was cooled and the green crystalline solid was collected by filtration, washed with acetic anhydride and ether and dried. Recrystallisation from acetic anhydride afforded the title compound (3.5 g), decomposes 240°–245° C. (cap.) without loss of crystalline form $\lambda$max (in ethanol) 245 ($\epsilon$60,470), 265.5 ($\epsilon$15,270) and 386 nm ($\epsilon$7706).

EXAMPLE 11

5,14-Dihydro-9,12-dihydroxbenz[5,6]isoindolo[2,1-b]isoquinoline-8,13-dione

Method A

To the compound of Example 5 (190 mg) was added trifluoroacetic acid (3 ml). The reaction mixture was allowed to stand at about 20° C. (17 h) and was then carefully diluted with water (30 ml). The solid was collected by filtration, washed with water (3×10 ml) and dried in vacuo. The crude product (160 mg) in dichloromethane (40 ml) was loaded onto a 25 g silica gel column packed in dichloromethane. The column was eluted with 5% (v/v) ethyl acetate in dichloromethane and fractions containing the major component (R$_f$=0.73) were evaporated to dryness to give the title compound as an orange solid (50 mg) m.p. >320° C. (dec);

Analysis Found: C, 72.1; H, 3.9; N, 4.1. C$_{20}$H$_{13}$NO$_4$ requires: C, 72.5; H, 4.0; N, 4.2%.

Method B

To the compound of Example 5 (790 mg) was added tetrahydrofuran (100 ml) and 2M hydrochloric acid (100 ml). The reaction mixture was heated under reflux at 78° C. (7.5 h) and was then diluted with water (100 ml). The solid was collected by filtration, washed with water (3×40 ml) and dried in vacuo. The crude product (565 mg) in dichloromethane (1000 ml) was loaded onto a 300 g silica gel column paced in dichloromethane. The column was eluted with 5% (V/v) ethyl acetate in dichloromethane and fractions containing the major component (R$_f$=0.75) were evaporated to dryness to give the title compound as an orange solid (393 mg) m.p. >320° C. (dec.);

Analysis Found: C, 72.4; H, 4.1; N, 4.0. C$_{20}$H$_{13}$NO$_4$ requires: C, 72.5; H, 4.0 N, 4.2%.

EXAMPLE 12

5,14-Dihydro-14-(2-propenyl)benz[5,6]isoindolo[2,1-b]isoquinoline-8,13-dione A mixture of Intermediate 1 (300 mg), potassium carbonate (690 mg), benzyl triethylammonium chloride (32 mg) and allyl bromide (0.20 ml) in acetonitrile (25 ml) was stirred and heated under reflux for 4 h. The mixture was cooled to room temperature, diluted with dichloromethane (200 ml) and filtered. The filtrate was evaporated to dryness and the residue was purified by column chromatography on silica gel eluting with chloroform to give the title compound (240 mg) m.p. 159°–160° C. Recrystallisation from carbon tetrachloride gave yellow needles (185 mg) m.p. 160°–162° C. $\lambda_{max}$ (in ethanol) 245 nm ($\epsilon=48190$) 265 nm ($\epsilon=17140$) and 370 nm ($\epsilon=6280$).

EXAMPLE 13

5,14-Dihydro-14-methylbenz[5,6]isoindolo[2,1-b]isoquinoline-8,13-dione

A mixture of 5,14-dihydrobenz[5,6]isoindolo[2,1-b]isoquinoline-8,13-dione (0.96 g) (Intermediate 1), benzyl triethylammonium chloride (0.16 g), potassium carbonate (2.20 g) and iodomethane (0.45 ml) in acetonitrile (100 ml) was stirred and heated under reflux for 4 h. A further portion of iodomethane (0.5 ml) was added and the mixture was stirred at 80° C. for 1 h. The mixture was cooled to room temperature, diluted with dichloromethane (250 ml) and filtered. The filtrate was concentrated in vacuo and the residue was purified on preparative plates eluting five times with chloroform to give the title compound (98 mg) m.p. 215°–218° C. $\lambda$max (in CHCl$_3$) 246.5 nm ($\epsilon$51,050), 266.5 nm ($\epsilon$18,250) and 366.55 nm ($\epsilon$3,700).

EXAMPLE 14

Suspension for parenteral administration. "Active ingredient" as used in the following may be for example the compound of Example 10.

| Active ingredient | 1000 mg |
|---|---|
| Tween 80 | 1000 mg |
| Dimethylformamide | 1000 ml |
| Fresh distilled water | 1000 ml |

Replacement Vehicle:

| Tween 80 | 50 mg |
|---|---|
| Sodium chloride | 900 mg |
| Fresh distilled water to | 100 ml |

Method of Preparation

Dissolve tween 80 (1000 mg) and the active ingredient (1000 mg) in the dimethylformamide. Add this solution to the fresh distilled water (1000 ml) using a radial Silverson fitted with an injection tube. Stir for 30 minutes. Pour the suspension into centrifuge tubes and centrifuge at 3000 rpm until the supernatant is clear. Decant the supernatant. Resuspend the "cake" with a portion of the replacement vehicle. Make up to 100 ml with replacement vehicle.

Toxicity

The compounds of the invention in general produce no significant toxic effects in mice at doses where they cause significant reduction in mean tumour weight. The compounds of Examples 9b and 9c for example produced no significant toxic effects when administered intraperitoneally to mice at doses up to some 50 mg/kg daily for up to twenty days.

We claim:

1. A pharmaceutical composition comprising a compound of formula (I)

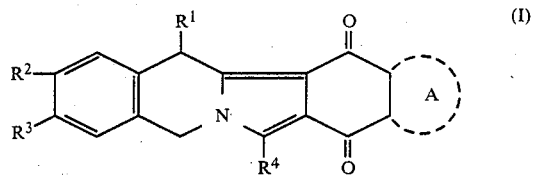

(wherein
$R^1$ represents a hydrogen atom or a $C_{1-4}$ alkyl, $C_{2-4}$ alkenyl or $C_{2-4}$ alkynyl group;
$R^2$ represents a hydrogen atom or a hydroxyl, $C_{1-4}$ alkoxy or $C_{2-4}$ alkanoyloxy group;
$R^3$ represents a hydrogen atom, or (when $R^2$ is other than a hydrogen atom) $R^3$ may also represent a hydroxyl, $C_{1-4}$ alkoxy or $C_{2-4}$ alkanoyloxy group, or $R^2$ and $R^3$ together represent a methylenedioxy group;
$R^4$ represents a hydrogen or halogen atom or a $C_{1-3}$ alkyl group or a phenyl group optionally substituted by a halogen atom or a hydroxy, $C_{1-4}$ alkyl, $C_{1-4}$ alkoxy or $C_{1-4}$ alkanoyloxy group; and
the ring A represents a group of formula

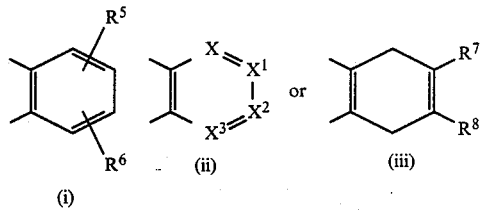

where $R^5$ and $R^6$ each represents a hydrogen atom or a hydroxyl, $C_{1-4}$ alkoxy or $C_{1-4}$ alkanoyloxy group, $R^7$ and $R^8$ each represents a hydrogen atom or a methyl group, and one of X, $X^1$, $X^2$ and $X^3$ represents a nitrogen atom and the others represent —CH— groups; with the proviso that where A represents a group of formula (i) at least one of $R^1$ to $R^6$ represents other than a hydrogen atom) together with at least one pharmaceutical carrier or excipient.

2. A composition as claimed in claim 1 containing a compound of formula (I) wherein $R^1$ represents a hydrogen atom or a methyl group, $R^2$ represents a hydrogen atom, $R^3$ represents a hydrogen atom, $R^4$ represents a hydrogen or bromine atom or a methyl group, and the ring A represents a group of formula

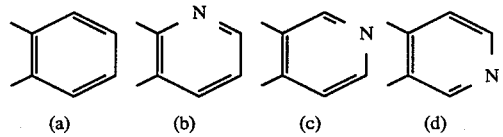

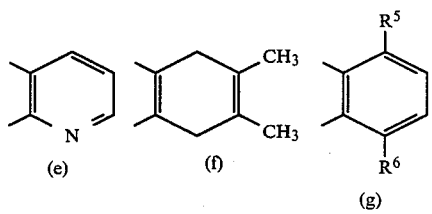

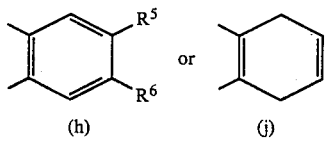

where one of R⁵ and R⁶ represents a hydrogen atom or a hydroxyl, methoxy or acetyloxy group, and the other represents a hydroxyl, methoxy or acetyloxy group.

3. A composition as claimed in claim 1 in dosage unit form containing from 50 to 1000 mg of the compound of formula (I).

4. A compound of formula (I)

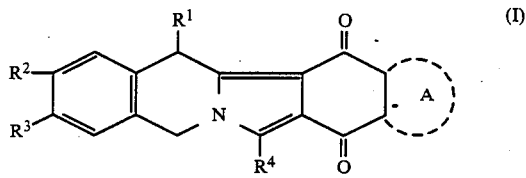

(wherein $R^1$ represents a hydrogen atom or a $C_{1-4}$ alkyl, $C_{2-4}$ alkenyl or $C_{2-4}$ alkynyl group;

$R^2$ represents a hydrogen atom or a hydroxyl, $C_{1-4}$ alkoxy or $C_{2-4}$ alkanoyloxy group;

$R^3$ represents a hydrogen atom, or (when $R^2$ is other than a hydrogen atom) $R^3$ may also represent a hydroxyl, $C_{1-4}$ alkoxy or $C_{2-4}$ alkanoyloxy group, or $R^2$ and $R^3$ together represent a methylenedioxy group;

$R^4$ represents a hydrogen or halogen atom or a $C_{1-3}$ alkyl group or a phenyl group optionally substituted by a halogen atom or a hydroxy, $C_{1-4}$ alkyl, $C_{1-4}$ alkoxy or $C_{1-4}$ alkanoyloxy group; and the ring A represents a group of formula

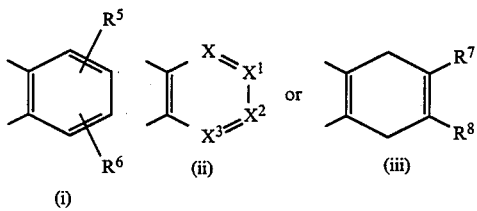

where $R^5$ and $R^6$ each represents a hydrogen atom or a hydroxyl, $C_{1-4}$ alkoxy or $C_{1-4}$ alkanoyloxy group, $R^7$ and $R^8$ each represents a hydrogen atom or a methyl group, and one of x, $x^1$, $x^2$ and $x^3$ represents a nitrogen atom and the others represent —CH— groups;

with the proviso that where A represents a group of formula (i) and $R^1$, $R^2$, $R^3$, $R^5$ and $R^6$ represent hydrogen atoms, $R^4$ represents a halogen atom, a $C_{2-3}$ alkyl group or a phenyl group optionally substituted by a halogen atom or a hydroxy, $C_{1-4}$ alkyl, $C_{1-4}$ alkoxy or $C_{1-4}$ alkanoyloxy group).

5. Compounds of formula (I) as claimed in claim 4 wherein $R^1$ represents a hydrogen atom or a methyl group, $R^2$ represents a hydrogen atom, $R^3$ represents a hydrogen atom, $R^4$ represents a hydrogen or bromine atom or a methyl group, and the ring A represents a group of formula

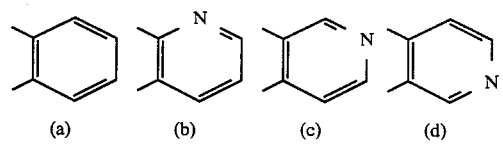

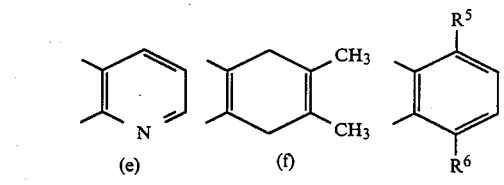

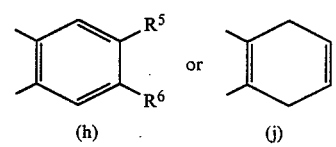

where one of $R^5$ and $R^6$ represents a hydrogen atom or a hydroxyl, methoxy or acetyloxy group, and the other represents a hydroxyl, methoxy or acetyloxy group.

6. A compound of formula (I) as claimed in claim 4 being a compound selected from the group consisting of:
(a)  5,14-dihydro-14-methylbenz[5,6]isoindolo[2,1-b]isoquinoline-8,13-dione;
(b)  5,14-dihydro-9-hydroxybenz[5,6]isoindolo[2,1-b]isoquinoline-8,13-dione;
(c)  5,14-dihydro-12-hydroxybenz[5,6]isoindolo[2,1-b]isoquinoline-8,13-dione;
(d)  5,14-dihydro-9-methoxybenz[5,6]isoindolo[2,1-b]isoquinoline-8,13-dione;
(e)  5,14-dihydro-12-methoxybenz[5,6]isoindolo[2,1-b]isoquinoline-8,13-dione;
(f)  7-bromo-5,14-dihydrobenz[5,6]isoindolo[2,1-b]isoquinoline-8,13-dione;
(g)  9,12-bis(acetyloxy)-5,14-dihydrobenz[5,6]isoindolo[2,1-b]isoquinoline-8,13-dione;
(h)  5,9,12,14-tetrahydrobenz[5,6]isoindolo[2,1-b]isoquinoline-8,13-dione; and
(i)  5,14-dihydro-9,12-dihydroxybenz[5,6]isoindolo[2,1-b]isoquinoline-8,13-dione.

* * * * *